(12) United States Patent
Bockholt et al.

(10) Patent No.: US 7,884,224 B2
(45) Date of Patent: Feb. 8, 2011

(54) METHOD FOR PRODUCING PHOSPHONATOSILANES

(75) Inventors: Andreas Bockholt, Munich (DE); Leonhard Brader, Fischbachau (DE)

(73) Assignee: Wacker Chemie AG, Munich (DE)

( * ) Notice: Subject to any disclaimer, the term of this patent is extended or adjusted under 35 U.S.C. 154(b) by 384 days.

(21) Appl. No.: 11/572,536

(22) PCT Filed: Jun. 23, 2005

(86) PCT No.: PCT/EP2005/006816

§ 371 (c)(1),
(2), (4) Date: Jan. 23, 2007

(87) PCT Pub. No.: WO2006/012952

PCT Pub. Date: Feb. 9, 2006

(65) Prior Publication Data

US 2008/0045735 A1   Feb. 21, 2008

(30) Foreign Application Priority Data

Jul. 29, 2004   (DE) .................. 10 2004 036 722

(51) Int. Cl.
C07F 9/02   (2006.01)
(52) U.S. Cl. ..................... 556/404; 556/479
(58) Field of Classification Search ................ 556/404, 556/479
See application file for complete search history.

(56) References Cited

U.S. PATENT DOCUMENTS 2,768,193 A    10/1956   Gilbert
3,700,760 A *  10/1972   Benghiat .................. 558/188
5,041,662 A     8/1991   Grambow et al.
5,087,741 A     2/1992   Tennant et al.
5,198,202 A     3/1993   Engel et al.

FOREIGN PATENT DOCUMENTS

| AT | 230874     | 12/1963 |
| CN | 1054233 A  | 9/1991  |
| CN | 1061955 A  | 6/1992  |
| GB | 1405289 A  | 9/1975  |
| JP | 48040723 A | 6/1972  |

OTHER PUBLICATIONS

Silverman, R.B. "The Organic Chemistry of Drug Design and Drug Action", Academic Press Inc. 1992, p. 19.*
Patbase Abstract corresponding to AT-B 230874, Dec. 30, 1963.
Ber. Stsch. Chem. Ges. 1898, 31, pp. 1048-1055.
Pure Appl. Chem. 1964, 9, pp. 307-335.
J. Polym. Sci., Part A: Polym. Chem. 2003, 41, pp. 48-59.
J. Chem. Soc. 1962, pp. 592-600.

* cited by examiner

*Primary Examiner*—Sudhakar Katakam
(74) *Attorney, Agent, or Firm*—Brooks Kushman P.C.

(57) ABSTRACT

In the preparation of phosphonatosilanes by reaction of organophosphites with halocarbon-functional silanes, the safety of the reaction is markedly increased while increasing space/time yield by continuously or periodically withdrawing reaction mixture, freeing the withdrawn mixture of phosphonatosilane product, and recycling the product-depleted remainder back to the reaction. Operation at temperatures of 100° C. or lower is made possible by this process.

15 Claims, No Drawings

METHOD FOR PRODUCING PHOSPHONATOSILANES

CROSS-REFERENCE TO RELATED APPLICATION

This application is the U.S. national phase of PCT Appln. No. PCT/EP 2005/006816 filed Jun. 23, 2005, which claims priority to German application 10 2004 036 722.1 filed Jul. 29, 2004.

BACKGROUND OF THE INVENTION

1. Field of the Invention

The invention relates to a process for preparing organosilicon compounds with phosphonate groups.

2. Description of the Related Art

Phosphonates can be prepared by the Arbuzov-Michaelis reaction (Ber. Dtsch. Chem. Ges. 1898, 31, 1048-1055; Pure Appl. Chem. 1964, 9, 307-335). In this reaction, haloalkanes or compounds which bear haloalkyl radicals are reacted with trialkyl phosphites. The preparation is effected in a batch process by mixing the reactants at high temperatures and subsequent distillation of the reaction mixture. In this way, it is also possible to prepare organosilicon compounds with phosphonate groups, referred to hereinafter as phosphonatosilanes, of the general formula (I),

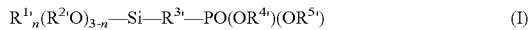  (I)

in which $R^{1\prime\prime}$ is an optionally halogen-substituted alkyl, cycloalkyl, alkenyl or aryl radical, $R^{2\prime}$ is an alkyl radical having 1-6 carbon atoms or an ω-oxaalkylalkyl radical having a total of 2-10 carbon atoms, $R^{3\prime}$ is an optionally substituted, branched or unbranched alkylene radical having 1-10 carbon atoms, $R^{4\prime}$ and $R^{5\prime}$ are each an optionally substituted alkyl, cycloalkyl, alkenyl or aryl radical, and n=0, 1, 2 or 3 (U.S. Pat. No. 2768193; J. Polym. Sci., Part A: Polym. Chem. 2003, 41, 48-59). For the preparation of these compounds, temperatures of >170° C. are generally required. Since the compounds described, however, are of low thermal stability (J. Chem. Soc. 1962, 592-600) and decompose exothermically at temperatures of T≧200° C., the achievable yields are limited. Moreover, a not inconsiderable endangerment potential results therefrom. Particularly for compounds of the formula I in which $R^3$ is a methylene unit, the preparation at reaction temperatures of T>100° C. is very problematic for safety reasons (100 K rule). When the reaction to prepare these compounds is conducted at reaction temperatures of T≦100° C., which presents fewer safety issues, the result is an uneconomic space-time yield.

The disadvantages of the known processes consist in the low space-time yields at low reaction temperatures and the restrictive yields at high reaction temperatures caused by the decomposition of the product, and the endangerment potential which originates from the exothermic decomposition reactions of the products.

SUMMARY OF THE INVENTION

It is an object of the invention to provide an economically viable process for preparing phosphonatosilanes at low reaction temperatures and with minimal formation of by-products. These and other objects are achieved through reaction at low tempereature accompanied by Optionally removing halocarbon byproduct volatilization from the reactor, and withdrawing A portion of the reaction mixture continuously or repeatedly, removing phoshonatosilane from the withdrawn mixture, and recycling the remnant back to the reactor.

The advantages of the process consist in the high space-time yields at low reaction temperatures and in the minimal formation of by-products compared to the known process. Further purigication of the product is therefore not necesssary in many cases. Moreover, the process is unproblematic from a safety point of view as a result of low process temperatures.

DETAILED DESCRIPTION OF THE PREFERRED EMBODIMENT(S)

The invention provides a process for preparing phosphanotosilanes of the general formula (II)

  (II)

in which halogenated silanes of the general formula (III)

  (III)

are reacted with phosphites of the general formula (IV)

$P(OR^4)(OR^5)(OR^6)$  (IV)

where
$R^1$ is an optionally halogen-substituted hydrocarbon radical having 1-20 carbon atoms or hydrogen,
X is a hydrolyzable group or OH,
$R^3$ is an optionally halogen-substituted alkylene radical having 1-10 carbon atoms,
$R^4$, $R^5$ and $R^6$ are each optionally halogen-substituted hydrocarbon radicals having 1-20 carbon atoms,
Hal is a halogen atom and
n is 0, 1, 2 or 3, in which a portion of the reaction mixture is withdrawn continuously or repeatedly during the reaction, freed of the product already formed and added back to the rest of the reaction mixture.

The advantages of the process consist in the high space-time yields at low reaction temperatures and in the minimal formation of by-products compared to the known process. Further purification of the product is therefore not necessary in many cases. Moreover, the process is unproblematic from a safety point of view as a result of the low process temperatures.

$R^1$ is preferably an optionally halogen-substituted alky, cycloalkyl, alkenyl or aryl radical preferably having from 1 to 10 carbon atoms, more preferably an alkyl radical having from 1 to 3 carbon atoms, especially methyl or ethyl.

$R^3$ is preferably an optionally substituted, branched or unbranched alkylene radical having from 1 to 6 carbon atoms, more preferably from 1 to 3 carbon atoms, especially methylene, ethylene, or n-propylene.

$R^4$, $R^5$ and $R^6$ are preferably optionally halogen-substituted alkyl, cycloalkyl, alkenyl or aryl radicals preferably having from 1 to 16 carbon atoms, more preferably alkyl radicals having from 1 to 6 carbon atoms, especially methyl, ethyl, or phenyl.

Halogen substituents on $R^1$ to $R^6$ are preferably fluorine or chlorine.

X is preferably an alkoxy group having from 1 to 3 carbon atoms or a halogen such as fluorine, chlorine, or bromine.

Hal is preferably bromine or chlorine.

The product is preferably withdrawn by repeated, and especially by continuous, withdrawal of an amount of the reaction mixture from the reaction vessel. Preferably 5-50% of the reaction mixture is withdrawn per hour. The subsequent separation of the reaction mixture into product and reactant is preferably effected by distillation, especially by applying the reaction mixture to a thin-film evaporator. The product is collected in the high boiler fraction, while the distillate is recycled into the reaction vessel. This is preferably done continuously. The volatile $R^6$-Hal by-product formed in the reaction is preferably withdrawn from the reaction mixture, preferably by distillation under reduced pressure. The overall process is preferably conducted continuously.

The process may be performed in the presence or in the absence of aprotic solvents. If aprotic solvents are used, preference is given to solvents or solvent mixtures having a boiling point or boiling range of up to 120° C. at 10013 mbar. Examples of such solvents are ethers such as dioxane, tetrahydrofuran, diethyl ether, diisopropyl ether, diethylene glycol dimethyl ether; chlorinated hydrocarbons such dichloromethane, trichloromethane, tetrachloromethane, 1,2-dichloro-ethane, trichloroethylene; hydrocarbons such as pentane, n-hexane, hexane isomer mixtures, heptane, octane, wash benzine, petroleum ether, benzene, toluene, xylenes; ketones such as acetone, methyl ethyl ketone, diisopropyl ketone, methyl isobutyl ketone (MIBK); esters such as ethyl acetate, butyl acetate, propyl propionate, ethyl butyrate, ethyl isobutyrate; carbon disulfide and nitrobenzene, or mixtures of these solvents.

The term solvent does not mean that all reaction products must dissolve therein. The reaction can also be performed in a suspension or emulsion of one or more reactants. The reaction can also be performed in a solvent mixture with a miscibility gap, at least one reactant being soluble in each of the mixed phases.

The process is performed preferably at temperatures of from 20° C. to 300° C., in particular from 50° C. to 200° C. The process is preferably performed with exclusion of air and moisture.

All above symbols in the above formulae are each defined independently of one another. In all formulae, the silicon atom is tetravalent.

EXAMPLE 1

Preparation of Diethylphosphonatomethyl-dimethoxymethylsilane

In a 2 l three-necked flask, a mixture of 618.7 g (4.0 mol) of chloromethyldimethoxymethylsilane and 664.6 g (4.0 mol) of triethyl phosphite are stirred at 100° C. at a pressure of 350 mbar for 2 hours, and the resultant ethyl chloride is collected in a cold trap. A constant volume of approx. 450 ml/h of the reaction mixture is then applied to a thin-film evaporator (p=20 mbar, T=100° C.) by means of a riser line. The diethylphosphonatomethyldimethoxymethylsilane is collected in the high boiler fraction, while the distillate is recycled into the reaction vessel via a pump. The volume of the reaction mixture is kept constant by the addition of reactant mixture. The yield of diethylphosphonatomethyldimethoxymethylsilane is 180 ml/h. The product is obtained in a purity of 95% (by GC). The reactants form the main impurities; by-products are found only in traces.

EXAMPLE 2

Preparation of Diethylphosphonatomethyl-methoxydimethylsilane

In a 2 l three-necked flask, a mixture of 554.6 g (4.0 mol) of chloromethylmethoxydimethylsilane and 664.6 g (4.0 mol) of triethyl phosphite are stirred at 100° C. at a pressure of 350 mbar for 4 hours, and the resultant ethyl chloride is collected in a cold trap. A constant volume of approx. 400 ml/h of the reaction mixture is then applied to a thin-film evaporator (p=20 mbar, T=100° C.) by means of a riser line. The diethylphosphonatomethylmethoxydimethylsilane is collected in the high boiler fraction, while the distillate is recycled into the reaction vessel via a pump. The volume of the reaction mixture is kept constant by the addition of reactant mixture. The yield of diethylphosphonatomethylmethoxydimethylsilane is 125 ml/h. The product is obtained in a purity of 96% (by GC). The reactants form the main impurities; by-products are found only in traces.

EXAMPLE 3

Preparation of Diethylphosphonatomethyl-trimethoxysilane

In a 2 l three-necked flask, a mixture of 682.7 g (4.0 mol) of chloromethyltrimethoxysilane and 664.6 g (4.0 mol) of triethyl phosphite are stirred at 100° C. at a pressure of 300 mbar for 4 hours, and the resultant ethyl chloride is collected in a cold trap. A constant volume of approx. 450 ml/h of the reaction mixture is then applied to a thin-film evaporator (p=5 mbar, T=100° C.) by means of a riser line. The diethylphosphonatomethyltrimethoxysilane is collected in the high boiler fraction, while the distillate is recycled into the reaction vessel via a pump. The volume of the reaction mixture is kept constant by the addition of reactant mixture. The yield of diethylphosphonatomethyltrimethoxysilane is 100 ml/h. The product is obtained in a purity of 96% (by GC). The reactants form the main impurities; by-products are found only in traces.

EXAMPLE 4

Preparation of Diethylphosphonatopropyl-trimethoxysilane

In a 2 l three-neck flask, a mixture of 1600 g (8.0 mol) of chloropropyltrimethoxysilane and 60 g of triethyl phosphite (0.4 mol) is heated to reflux. The temperature of the reaction mixture is then adjusted to 180° C. by adding further triethyl phosphite. The mixture is stirred at this temperature for 6 hours. A constant volume of approx. 250 ml/h of the reaction mixture is then applied to a thin-film evaporator (p=5 mbar, T=180° C.) by means of a riser line. The diethyl-phosphonatopropyltrimethoxysilane is collected in the high boiler fraction, while the distillate is recycled into the reaction vessel by a pump. The volume of the reaction mixture is kept constant by the addition of reactant mixture. The yield of diethylphosphonato-propyltrimethoxysilane is 60 ml/h. The product is obtained in a purity of 90% (by GC). After a further thin-film evaporator step, the product is obtained in a purity of 97% (by GC). The reactants form the main impurities; by-products are found only in traces.

NONINVENTIVE COMPARATIVE EXAMPLE

Preparation of diethylphosphonatomethyltrimethoxysilane

In a 500 ml three-neck flask, a mixture of 102.4 g (0.6 mol) of chloromethyltrimethoxysilane and 99.7 g (0.6 mol) of triethyl phosphite is heated at 100° C. for 50 hours. All volatile constituents are then distilled off at 100° C. under reduced pressure (0.1 mbar). 132.1 g of diethylphosphonatomethyltrimethoxysilane are obtained in a purity of 94% (by GC, 0.46 mol, yield 76% of theory).

The invention claimed is:

1. A process for preparing phosphonatosilanes of the formula (II)

$$R^1_n(X)_{3-n}\text{—Si—}R^3\text{—PO}(OR^4)(OR^5) \quad (II)$$

comprising reacting halogenated silanes of the formula (III)

$$R^1_n(X)_{3-n}\text{—Si—}R^3\text{—Hal} \quad (III)$$

with phosphites of the formula (IV)

$$P(OR^4)(OR^5)(OR^6) \quad (IV)$$

in a reaction vessel,
where
$R^1$ is an optionally halogen-substituted hydrocarbon radical having 1-20 carbon atoms or hydrogen,
X is a hydrolyzable group or OH,
$R^3$ is an optionally halogen-substituted alkylene radical having 1-10 carbon atoms,
$R^4$, $R^5$ and $R^6$ are each optionally halogen-substituted hydrocarbon radicals having 1-20 carbon atoms,
Hal is a halogen atom and
n is 0, 1, 2 or 3,
in which a portion of the reaction mixture is withdrawn continuously or repeatedly during the reaction, separating the product formed from the reactants by applying the reaction mixture to a thin-film evaporator, separating a bottoms high boiler fraction containing product, and recycling distillate to the reaction vessel.

2. The process of claim 1, wherein $R^1$ is an alkyl radical having from 1 to 3 carbon atoms or hydrogen.

3. The process of claim 1, wherein $R^3$ is selected from the group consisting of methylene, ethylene, and n-propylene.

4. The process of claim 2, wherein $R^3$ is selected from the group consisting of methylene, ethylene, and n-propylene.

5. The process of claim 1, wherein $R^4$, $R^5$ and $R^6$ are each an alkyl radical having from 1 to 6 carbon atoms or a phenyl.

6. The process of claim 2, wherein $R^4$, $R^5$ and $R^6$ are each an alkyl radical having from 1 to 6 carbon atoms or a phenyl.

7. The process of claim 3, wherein $R^4$, $R^5$ and $R^6$ are each an alkyl radical having from 1 to 6 carbon atoms or a phenyl.

8. The process of claim 1, wherein each X independently is an alkoxy group having from 1 to 3 carbon atoms, or is fluorine, chlorine or bromine.

9. The process of claim 2, wherein each X independently is an alkoxy group having from 1 to 3 carbon atoms, or is fluorine, chlorine or bromine.

10. The process of claim 3, wherein each X independently is an alkoxy group having from 1 to 3 carbon atoms, or is fluorine, chlorine or bromine.

11. The process of claim 5, wherein each X independently is an alkoxy group having from 1 to 3 carbon atoms, or is fluorine, chlorine or bromine.

12. The process of claim 1, in which reaction mixture is withdrawn continuously.

13. The process of claim 1, in which the entire process is conducted continuously.

14. The process of claim 1, which is conducted at a temperature below 200° C. and at a pressure where halocarbon $R^4$-Hal volatizes from the reaction mixture.

15. The process of claim 1, which is conducted at a temperature at about 100° C. or lower and at a pressure where halocarbon $R^4$-Hal volatizes from the reaction mixture.

* * * * *